(12) United States Patent
Giuliani et al.

(10) Patent No.: US 9,386,777 B2
(45) Date of Patent: Jul. 12, 2016

(54) PROCESS OF MICROBIC BIOTECHNOLOGY FOR COMPLETELY DEGRADING GLUTEN IN FLOURS

(75) Inventors: Giammaria Giuliani, Milan (IT); Anna Benedusi, Milan (IT); Raffaella Di Cagno, Milan (IT); Carlo Giuseppe Rizzello, Bari (IT); Maria De Angelis, Bari (IT); Marco Gobbetti, Bari (IT); Angela Cassone, Bari (IT)

(73) Assignee: Giuliani S.P.A., Milan (IT)

( * ) Notice: Subject to any disclaimer, the term of this patent is extended or adjusted under 35 U.S.C. 154(b) by 217 days.

(21) Appl. No.: 13/131,458

(22) PCT Filed: Dec. 17, 2009

(86) PCT No.: PCT/IT2009/000569
§ 371 (c)(1),
(2), (4) Date: Oct. 13, 2011

(87) PCT Pub. No.: WO2010/073283
PCT Pub. Date: Jul. 1, 2010

(65) Prior Publication Data
US 2012/0034339 A1    Feb. 9, 2012

(30) Foreign Application Priority Data
Dec. 23, 2008  (IT) .............................. RM2008A0690

(51) Int. Cl.
*A21D 8/04*      (2006.01)
*A23L 1/03*      (2006.01)
*A21D 13/06*     (2006.01)
(Continued)

(52) U.S. Cl.
CPC .............. *A21D 8/042* (2013.01); *A21D 13/066* (2013.01); *A23L 1/034* (2013.01); *C12N 1/20* (2013.01); *C12R 1/225* (2013.01); *C12R 1/25* (2013.01); *C12Y 304/11* (2013.01); *C12Y 304/11005* (2013.01)

(58) Field of Classification Search
CPC .............. A21D 13/066; C12Y 304/14; C12Y 304/11005; C12Y 304/11; C12R 1/25
See application file for complete search history.

(56) References Cited

U.S. PATENT DOCUMENTS 2,215,957 A  *  9/1940  Freilich et al. .................. 426/19
6,132,710 A  *  10/2000  Panigrahi et al. .......... 424/93.45
(Continued)

FOREIGN PATENT DOCUMENTS

| JP | 2008-532532 A | 8/2008 |
| JP | 2012-513198 A | 6/2012 |

(Continued)

OTHER PUBLICATIONS

Derwent Abstract of EP 1258526 May 16, 20013 pages.*
(Continued)

*Primary Examiner* — Felicia King
(74) *Attorney, Agent, or Firm* — Arent Fox LLP (57) ABSTRACT

The present invention concerns the use of lactic acid bacteria selected and fungal enzymes for the gluten complete degradation from both bread and durum wheat, barley, rye and oat flour. In particular, the invention concerns the use of lactic acid bacteria selected and fungal enzymes for the gluten complete degradation (residual gluten concentration lower than 20 ppm) of cereal flours, which after detoxification can be used according to a standardized biotechnological protocol for the production of various gluten-free foods.

7 Claims, 7 Drawing Sheets

(51) Int. Cl.
  C12N 1/20    (2006.01)
  C12R 1/225   (2006.01)
  C12R 1/25    (2006.01)

(56) References Cited

U.S. PATENT DOCUMENTS

2004/0005348 A1* 1/2004 Vincent et al. .............. 424/442
2008/0003265 A1* 1/2008 Casey et al. ................. 424/439
2008/0131556 A1  6/2008 De Simone et al.

FOREIGN PATENT DOCUMENTS

| WO | WO 2006/097415 A1 | 9/2006 |
| WO | WO 2008/010252 A2 | 1/2008 |
| WO | WO 2008/010252 A2 | 1/2008 |
| WO | WO 2010/073283 A2 | 7/2010 |

OTHER PUBLICATIONS

Gerez et al. "Gluten breakdown by lactobacillus and pedicocci strains isolated from sourdough" 2006 Letters in Applied Microbiology vol. 42 pp. 459-464.*
A. Corsetti et al., "Combined Effect of Sourdough Lactic Acid Bacteria and Additives on Bread Firmness and Staling," J. Agric. Food Chem., vol. 48, No. 7, pp. 3044-3051 (2000).
Raffaella Di Cagno et al., "Use of Selected Sourdough Strains of *Lactobacillus* for Removing Gluten and Enhancing the Nutritional Properties of Gluten-Free Bread," Journal of Food Protection, vol. 71, No. 7, pp. 1491-1495 (2008).
S. Coppola et al., "Effect of leavening microflora on pizza dough properties," Journal of Applied Microbiology, vol. 85, pp. 891-897 (1998).
M.M. Moore et al., "Sourdough fermented by *Lactobacillus plantarum* FST 1.7 improves the quality and shelf life of gluten-free bread," Eur. Food Res. Technol., vol. 226, pp. 1309-1316 (2008).
M.M. Moore et al., "Effect of Lactic Acid Bacteria on Properties of Gluten-Free Sourdoughs, Batters, and Quality and Ultrastructure of Gluten-Free Bread," Cereal Chem. Vo. 84, No. 4, pp. 357-364 (2007).
Di Cagno, Raffaella et al., "Use of Selected Sourdough Strains of Lactobacillus for Removing Gluten and Enhancing the Nutritional Properties of Gluten-Free Bread", J. Food Protection, vol. 71, No. 7, pp. 1491-1495 (2008).
Australian First Examination Report dated Oct. 17, 2013 issued in Australian Patent Application No. 2009332504.
Bini et al., "Protein expression profiles in human breast ductal carcinoma and histologically normal tissue", Electrophoresis, vol. 18, pp. 2832-2841 (1997).
Canadian Office Action dated Mar. 12, 2013 issued in Canadian Patent Application No. 2,743,599.
Canadian Office Action dated May 15, 2014 issued in Canadian Patent Application No. 2,743,599.
Canadian Office Action dated Oct. 17, 2014 issued in Canadian Patent Application No. 2,743,599.
Canadian Office Action dated Sep. 30, 2013 issued in Canadian Patent Application No. 2,743,599.
Chen et al., "Identification and Characterization of Lactobacillus helveticus PepO2, an Endopeptidase with Post-Proline Specificity", Appl Environ Microbiol, vol. 69, pp. 1276-1282 (2003).
Chinese Office Action dated Oct. 18, 2013 issued in Chinese Patent Application No. 200980152930.6.
De Angelis et al., "VSL#3 probiotic preparation has the capacity to hydrolyze gliadin polypeptides responsible for Celiac Sprue", Biochim Biophys Acta, vol. 1762, pp. 80-93 (2006).
Di Cagno et al., "Pasta Made from Durum Wheat Semolina Fermented with Selected Lactobacilli as a Tool for a Potential Decrease of the Gluten Intolerance", J Agr Food Chem, vol. 53, pp. 4393-4402 (2005).
Di Cagno et al., "Proteolysis by Sourdough Lactic Acid Bacteria: Effects on Wheat Flour Protein Fractions and Gliadin Peptides Involved in Human Cereal Intolerance", Appl Environ Microbiol, vol. 68, pp. 623-633 (2002).
Di Cagno et al., "Sourdough Bread Made from Wheat and Nontoxic Flours and Started with Selected Lactobacilli is Tolerated in Celiac Sprue Patients", Appl Environ Microbiol vol. 70, pp. 1088-1096 (2004).
Gobbetti et al., "Study of the effects of temperature, pH, NaCL, and aw on the proteolytic and lipolytic activities of cheese-related lactic acid bacteria by quadratic response surface methodology", Enzyme Microbiol Technol, vol. 25, pp. 795-809 (1999).
Gobbetti et al., "The sourdough microflora: Interactions of lactic acid bacteria and yeasts", Food Sci Technol, vol. 9, pp. 267-274 (1998).
Grehn et al., "Dietary habits of Swedish adult coeliac patients treated by a gluten-free diet for 10 years", Scand J Nutr, vol. 45, pp. 178-182 (2001).
Hamer, "Coeliac Disease: Background and biochemical aspects", Biotechnol Advanc, vol. 23, pp. 401-408 (2005).
Japanese Office Action dated Jun. 2, 2014 issued in Japanese Patent Application No. 2011-541720.
Japanese Office Action dated Sep. 10, 2013 issued in Japanese Patent Application No. 2011-541720.
Mariani et al., "The Gluten-Free Diet: A Nutritional Risk Factor for Adolescents with Celiac Disease?", J Pediart Gastroenterol Nut, vol. 27, pp. 519-523 (1998).
Mexican Office Action dated Sep. 26, 2012 issued in Mexican Patent Application No. MX/a/2011/005466.
New Zealand Office Action dated Aug. 3, 2011 issued in New Zealand Patent Application No. 593374.
New Zealand Office Action dated Feb. 12, 2013 issued in New Zealand Patent Application No. 593374.
New Zealand Office Action dated Nov. 16, 2012 issued in New Zealand Patent Application No. 593374.
Rewers, "Epidemiology of Celiac Disease: What Are the Prevalence, Incidence, and Progression of Celiac Disease?" Gastroenterology, vol. 128, pp. 47-51 (2005).
Rizzello et al., "Highly Efficient Gluten Degradation by Lactobacilli and Fungal Proteases during Food Processing: New Perspectives for Celiac Disease", Appl Environ Microbiol, vol. 73, No. 14, pp. 4499-4507 (2007).
Russian Office Action dated Feb. 18, 2015 issued in Russian Patent Application No. IAP20110322.
Russian Office Action dated Feb. 21, 2013 issued in Russian Patent Application No. 2011130911.
Sollid et al., "Future therapeutic options for celiac disease", Gastroenterol. Hepatol., vol. 2, pp. 140-147 (2005).
Stepniak et al., "Highly efficient gluten degradation with a newly identified prolyl endoprotease: implications for celiac disease", Am J Physiol Gastrointest Liver Physiol, vol. 291, pp. G621-G629 (2006).
Stern et al., "Analysis and clinical effects of gluten in coeliac disease.", Eur J Gastroenetrol Hepatol, vol. 13, pp. 741-747 (2001).
Thompson et al., "Gluten-free diet survey: are Americans with coeliac disease consuming recommended amounts of fibre, iron, calcium and grain foods?", J Human Nutr Diet, vol. 18, pp. 163-169.
Valdes et al., "Innovative approach to low-level gluten determination in foods using a novel sandwich enzyme-linked immunosorbent assay protocol", Eur J Gastroenterol Hepatol, vol. 15, pp. 465-474 (2003).

* cited by examiner

PROCESS OF MICROBIC BIOTECHNOLOGY FOR COMPLETELY DEGRADING GLUTEN IN FLOURS

CROSS-REFERENCED TO RELATED APPLICATION

This application is a national Stage entry of International Application No. PCT/IT2009/000569, filed Dec. 17, 2009, which claims priority to Italian Patent Application No. RM2008A000690, filed Dec. 23, 2008, the duty of disclosure of the prior application in its entirety by reference.

The present invention concerns a microbic biotechnology for completely degrading gluten in flours. Particularly, the process according to the invention involves the use of selected lactic bacteria and fungal proteases routinely used for the manufacture of leavened baked goods, under liquid fermentation conditions for the complete gluten degradation (residual gluten concentration lower than 20 ppm). Cereal flours resulting from fermentation process can be used as raw material for the production of gluten-free foods designed to be eaten by celiac patients. Proposed biotechnological process results in various economic, social, nutritional and sensory advantages compared to current production process of gluten-free foods made by ingredients which are naturally gluten-free or as result of extraction processes.

Gluten intolerance epidemiology or celiac disease is continuously growing. Last surveys about European and the United States population report an incidence of 1/100 affected individuals (Rewers, 2005. Epidemiology of celiac disease; what are the prevalence, incidence, and progression of celiac disease. *Gastroenterology* 128:47-51). According to current knowledge, unique effective therapeutic remedy against this alimentary intolerance is a completely gluten-free diet to be observed rigorously for all the life (Hamer, 2005. Celiac Disease: Background and biochemical aspects. *Biotechnol Advanc* 23:401-408). It is known, for example, the use of lactic bacteria for the preparation of baked goods from gluten-free flours (More et al. Cereal Chemistry, American Association of Cereal Chemists. Minneapolis, US, vol. 84, no. 4, 1 Jan. 2007, pp. 357-364 and Moore et al., European Food Research and Technology, vol. 226, 6 Jun. 2007, pp. 1309-1316). However, the gluten-free diet results also in apparent disadvantages. It is very expensive, gluten-free products, when compared to cereal based products, display lower sensory quality and storage, the diet is difficult to be strictly observed and it needs to be continuously monitored by dieticians, also taking in consideration nutritional imbalances (for example fibres, minerals and vitamins) resulting from complete absence of cereals in the feeding (Grehn et al., 2001. Dietary habits of Swedish adult coeliac patients treated by a gluten-free diet for 10 years. *Scand J Nutr* 45: 178-182; Mariani et al., 1998. The gluten-free diet: a nutritional risk factor for adolescents with celiac disease. *J Pediart Gastroenterol Nut* 27: 519-523; Thompson et al., 2005. Gluten-free diet survey: are Americans with celiac disease consuming recommended amounts of fibre, iron, calcium and grain foods? *J. Human. Nutr. Diet.* 18:163-169). Moreover, in some cases (for example "refractory sprue") also the complete observance of gluten-free diet does not allow a complete recovery of the intestinal functionality (Sollid and Khosla, 2004. Future therapeutic options for celiac disease. *Gastroenterol. Hepatol.* 2:140-147). Within gluten-free diet alternative therapeutic treatments, various studies have taken advantage of current knowledge on the sequences of toxic epitopes and have considered the use of microbial enzyme, particularly prolyl-endopeptidase (PEPs), for the hydrolysis of these polypeptides. Microbial enzymes have been suggested as diet supplements (Shan et al., 2004. Comparative biochemical analysis of three bacterial prolyl-endopeptidases: implications for celiac sprue. *Biochem. J.* 383:311-318) and/or for gluten in vitro detoxification (Chen et al., 2003. Identification and characterization of *Lactobacillus helveticus* PePO2, an endopeptidase with post-proline specificity. *Appl. Environ. Microbiol.* 69:1276-1282; Stepniak et al., 2005. Highly efficient gluten degradation with a newly identified prolyl-endoprotease: implications for celiac disease. *Am. J. Physiol. Gastrointest. Liver Physiol.* 291:G621-G629).

Patent application WO2008/010252 and Cagno et al. (Journal of Food Protection, vol. 71, no. 7, 2008, pp. 1491-1495) disclose a process for the preparation of baked goods from gluten-free flours and aiming to improve the nutritional, sensory and storage characteristics of these products prepared from gluten-free ingredients.

During the last few decades also the biotechnology of leavened baked goods is considerably changed, influencing the nutritional habits of entire populations previously subjected to a gluten based diet. Currently, leavened baked goods are manufactured by means of extremely rapid technological processes (for example, chemical leavening agents or using baker's yeast), completely replacing long fermentation processes using wild lactic acid bacteria and yeasts originated from raw materials, and used as "sourdoughs". By means of current processes the cereal components (for example proteins) are not subjected to any hydrolytic activity during food processing, maintaining the raw material characteristics (Gobbetti, 1998. The sourdough microflora: interactions between lactic bacteria and yeasts. *Trends Food Sci. Technol.* 9:267-274). Based on these considerations and taking advantage of enzyme potentialities of a mixture of selected lactic bacteria, various studies (Di Cagno et al., 2002, proteolysis by sourdough lactic bacteria: effects on wheat flour protein fractions and gliadin peptides involved in human cereal intolerance. *Appl. Environ. Microbiol.* 68:623-633; Di Cagno et al., 2004. Sourdough bread made from wheat and non toxic flours and started with selected lactobacilli is tolerated in celiac sprue patients. *Appl. Environ. Microbiol.* 70:1088-1096; Di Cagno et al., 2005. Pasta made from durum wheat semolina fermented with selected lactobacilli as a tool for a potential decrease of the gluten intolerance. *J. Agr. Food Chem.* 53:4393-4402; De Angelis et al., 2005. VSL#3 probiotic preparation has the capacity to hydrolyze gliadin polypeptides responsible for celiac sprue. *Biochim. Biophys. Acta.* 1762:80-93) demonstrated that using a traditional biotechnology, based on the use of selected lactic acid bacteria and long fermentation times, it is possible to reduce remarkably the initial cereal gluten concentration.

Codex Alimentarius, adopted by WHO (World Health Organization) and FAO (Food and Agricultural Organization), distinguishes "gluten-free products", containing ingredients with gluten concentration lower than 20 ppm, and "gluten-free made products", having a residual gluten concentration lower than 200 ppm. However, various studies, culminated with guidelines as issued by "Prolamins Working Group", suggest, in any case, a gluten threshold lower than 20 ppm to be maintained (Stern et al., 2001. Analysis and clinical effects of gluten in celiac disease. *Eur. J. Gastroenterol. Hepatol.* 13:741-747). A recent study by Rizzello et al. (Rizzello et al., 2007. Highly efficient gluten degradation by lactobacilli and fungal proteases during food processing: new perspectives for celiac disease. *Appl. Environ. Microbiol.* 73:4499-4507) considered the use of a more complex mixture consisting of 10 selected lactic acid bacteria, fungal proteases and long fermentation times (48 h at 37° C.), under semiliquid kneading conditions. According to electrophoretic, chromatographic and immunological analyses, the gluten contained in the wheat flour was degraded to a concentration lower than 20 ppm threshold.

It is further known Patent Application WO2006/097415 wherein, analogously to above mentioned study, a process for gluten degradation by means of the use of a complex mixture consisting of at least six lactic acid bacteria and/or bifidobacteria and long fermentation times (24-31 hours) is described. However, the method described in this document is not suitable in order the gluten to be completely degraded; therefore it results the impossibility for the administration to celiac patients. FIG. 1B of Patent Application WO2006/097415, in fact, shows that, after hydrolysis by means of microorganisms, there are yet clear spots for not degraded gliadins and this is confirmed in table 2, again from the same document, from which it is apparent that while some gliadins are partially hydrolysed others are not sensitive to hydrolysis process.

Based on literature and previously described data, some problems appear to be of major concern for the manufacture of gluten-free foods from detoxified cereal flour: (i) to simplify the composition of selected lactic bacteria to be used for the degradation process; (ii) to reduce considerably fermentation times thus making suitable to be used in industrial processes; to demonstrate the ability of lactic acid bacteria and fungal enzymes in order to act effectively on bread and durum wheat flours belonging to different varieties, and on barley, rye and oat; (iv) to provide a biotechnological process for gluten hydrolysis allowing detoxified cereal flours for the production of gluten-free products to be used; and (v) to demonstrate, by means of in vivo chronic medical trials, the absolute tolerance for celiac patients after extended administration of gluten-free products based on detoxified wheat flour.

In the light of above, it is therefore apparent the need to provide materials and methods for the preparation of gluten-free baked goods made of detoxified cereal flour which do not display, on one side, the disadvantages emerged from economic, social, nutritional and sensory survey of literature data and, on the other hand, the disadvantages of the currently commercially available gluten-free products.

The Authors of the present invention now observed that using only two selected lactic acid bacteria, in combination with fungal proteases, the fermentation times needed for gluten degradation are remarkably decreased. Moreover, the ability of lactic acid bacteria and fungal proteases for the complete gluten degradation from different bread and durum wheat varieties, barley, rye and oat flours was proved; a biotechnological protocol for the production of various leavened baked goods from detoxified wheat flour was provided; and the absolute product tolerance for celiac patients was demonstrated, thus allowing, in a completely innovative way, the wheat flour to be used as an ingredient for the manufacture of gluten-free leavened baked goods.

Lactic acid bacteria according to the present invention belong to the *Lactobacillus* genus and were isolated from "sourdoughs" used for the manufacture of Southern Italy typical breads. *Lactobacillus sanfranciscensis* DPPMA12 (deposited as DSMZ N. DSM22063 on 28 Nov. 2008) and *Lactobacillus plantarum* DPPMA125 (deposited as DSMZ N. DSM22064 on 28 Nov. 2008).

A biotechnological protocol involving the use of selected lactic acid bacteria and fungal proteases in an extremely rapid fermentation process (12-20 h at 30-37° C.) of cereal flours re-suspended in water at 20-50% weight and successive use thereof, at various percentages according to the desired characteristics, as an ingredient for a short leavening (about 1-3 h) by means of baker's yeast, for the production of gluten-free leavened baked goods (residual gluten content lower than 20 ppm) was standardized and optimized.

Below an outline of the biotechnological protocol for the production of leavened baked goods from detoxified gluten-free wheat flour is reported.

Culturing, washing and water suspension of lactic acid bacteria cultures

↓

Mixing of grain flour (30%) with water (70%) containing two selected lactic acid bacteria (cell density $10^8$ cfu/g) and fungal proteases (400 ppm each)

↓

Fermentation for 18 h at 37° C.

↓

Mixing with native maize (10%), rice flour (10%), egg (5%), sugar (3%), butter (1%) and baker's yeast (1.5%)

↓

Fermentation for 1.5 h at 30° C.

↓

Baking at 250° C. for 50 min

According to one of possible formulations, baked goods, containing 10 g equivalent of initial gluten, were daily administered to celiac patients over a period of 60 days. Immunochemical and histological assays proved the absolute tolerance of preparation from detoxified gluten-free flour.

According to complementary analyses using electrophoretic, chromatographic and immunological techniques, the fermentation process by means of selected lactic acid bacteria, not used in previous studies, and fungal proteases, according to the present invention, allows: (i) complete gluten detoxification (residual gluten content lower than 20 ppm); (ii) production of hydrolyzed flour consisting of a mixture of low molecular weight peptides and, especially, amino acids (ca. 15.000 mg/kg with respect to <1000 mg/kg in wheat flour) which increased the nutritional features with respect to conventional gluten-free products; (iii) remarkable reduction of process times compared to literature reported data, thus making said process suitable to an industrial scaling up transformation; (iv) production of gluten-free baked goods with different ingredient formulations involving the use of detoxified wheat flour at different concentrations (20-50%); and (v) absolute tolerance of the preparation for celiac patients after extended administration, according to first time reported medical data.

Products obtainable according to the process of the present invention display advantageous sensory, rheological and chemical properties not offered by prior art products (gluten-free products obtained from naturally gluten-free flours). Products according to the invention, in fact, maintain the nutritional properties of gluten containing flours thus offering better nutritional characteristics compared to products obtained from gluten-free flours.

Figure 5:
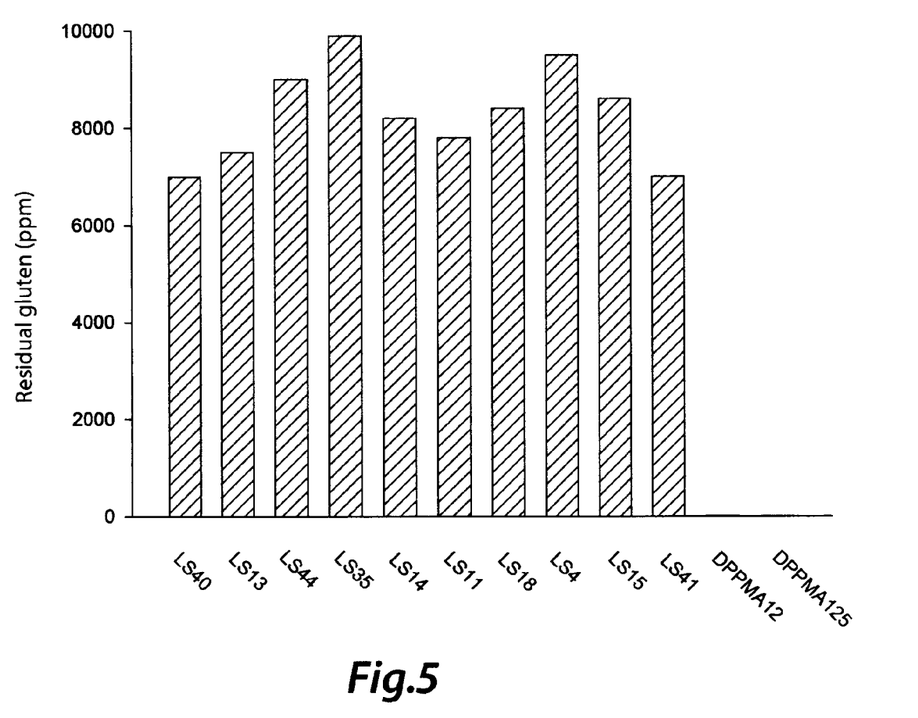
FIG. 5 shows the residual gluten concentration (ppm) in fermented doughs from *Lactobacillus sanfranciscensis* LS40, LS13, LS44, LS35, LS14, LS11, LS18, LS4, LS15 and LS41 (WO2008/010252) and from *L. sanfranciscensis* DPPMA12 (DSM22063) and *Lactobacillus plantarum* DPPMA125 (DSM22064) for 12 h at 37° C.

Moreover, the products according to the invention are completely gluten-free as result of gluten degradation process carried out by inventive lactic acid bacteria, otherwise than products obtained using known lactic acid bacteria (WO2006/097415, WO 2008/010252). Lactic acid bacteria according to Patent Application WO 2008/010252 were used under the same conditions of lactic acid bacteria according to the present invention and were not suitable to gluten degradation, in fact residual gluten content are on the order of ca. 6000-10000 ppm (FIG. 5). Therefore said bacteria can be used only for decontamination of gluten traces but they do not display same performances of bacteria according to the present invention.

With respect to the paper by Rizzello et al. (*Appl. Environ. Microbiol.* 73:4499-4507, 2007), the possibility to obtain a complete gluten degradation over remarkably shorter times (18 h compared to 48 h) implies, firstly, a considerable technological advantage making the transformation process comparable to the most frequent and common industrial processes for oven products. A too long (48 h) fermentation process, in addition to increase the technological costs, could present hygienic-sanitary risks. Further a more rapid gluten degradation process unavoidably results in the production of a raw material (flour with completely hydrolysed gluten) characterized by a different profile of free amino acids and, therefore, suitable to result in different sensory characteristics of gluten-free products compared to a longer process characterized by unavoidably different enzymatic kinetics.

It is therefore a specific object of the present invention a mixture comprising or consisting of *Lactobacillus sanfranciscensis* DSM22063 and *Lactobacillus plantarum* DSM 22064 lactic acid bacteria. The mixture can further comprise fungal proteolytic enzymes, as for example *Aspergillus oryzae, Aspergillus niger* proteases or mixtures thereof.

It is a further object of the present invention the use of as above defined mixture for the complete degradation of the gluten in both bread and durum wheat, barley, rye and oat flours.

The present invention further refers to a process for the preparation of a liquid flour dough with completely degraded gluten suitable to the production of leavened gluten-free products comprising or consisting of the following steps:
a) culture propagating of *Lactobacillus sanfranciscensis* DSM22063 and *Lactobacillus plantarum* DSM 22064 lactic acid bacteria;
b) flour mixing at concentrations of 20-50%, preferably 30%, and water at concentration of 50-80%, preferably 70%, containing the mixture of two bacteria of a) step at cell density of ca. $10^8$ cfu/g;
c) adding one or more fungal proteases each at concentration of 200-500 ppm, preferably 400 ppm;
d) fermenting for 8-20 h, preferably 12 h, at 30-37° C.

The process can further comprise a step e) of drying of liquid dough obtained in step d). Among the flours suitable to be used in the process there are both bread and durum wheat, barley, rye, oat flours or mixtures thereof, preferably bread and durum wheat.

Fungal proteolytic enzymes can be selected from the group consisting of *Aspergillus oryzae, Aspergillus niger* proteases or mixtures thereof.

Therefore, the invention also refers to a liquid or dried flour dough wherein the gluten is completely degraded according to as above defined process.

It is a further object of the invention a mixture comprising or consisting of as above defined dough in combination with one or more naturally gluten-free flours, as for example, those selected from the group consisting of native maize, white maize, rice, quinoa, teff or amaranth, and buckwheat flours. Particularly, above mentioned flours can be used according to the following percentages: native maize 5-15%, preferably 10%, white maize 5-15%, preferably 10%, rice, quinoa, teff or amaranth 10-30%, preferably 20%, and buckwheat flour 1-10%, preferably 5%, wherein said percentages are expressed by weight based on the total weight of the flour composition. Other ingredients that can be added to the formulation for gluten-free baked goods based on detoxified wheat flour are, for example, sugar, butter, egg and animal liquid cream.

It is a further object of the invention a process for the preparation of leavened baked goods by using of gluten detoxified flour according to as above defined process comprising or consisting of the following steps:
a) add a mixture of naturally gluten-free flours at 10-40%, preferably 30%, baker's yeast 1-2%, salt 0.1-1.0% and structuring agents 0.5-1% to gluten detoxified liquid flour dough using as above defined process and knead;
b) allow the fermentation to occur for approximately 1-3 h, preferably 1.5 h, at 30° C.;
c) bake for 50 minutes at 220° C. Where gluten detoxified flour dough is dried, the ingredient to water % ratio will be approximately 1.2:0.8.

The naturally gluten-free flours can be selected from the group consisting of native maize, white maize, rice, quinoa, teff, amaranth, buckwheat flour or mixtures thereof. On the other hand the gluten detoxified flour can be selected from the group consisting of both bread and durum wheat, barley, rye, oat flour and mixtures thereof, preferably bread or durum wheat flour.

Therefore, it is an object of the present invention also leavened baked goods obtainable by means of as above defined process.

A further object of the present invention is the process for the preparation of leavened baked goods comprising or consisting of the following steps:
a) add directly native maize, rice flour, egg, sugar, butter and baker's yeast to gluten detoxified flour dough according to as above defined process and knead;
b) allow the fermentation to occur for 1.5 h at 30° C. and
c) bake the leavened dough for 50 minutes at 250° C.

Particularly, in step a) the ingredient % are as below: native maize 10%, rice flour 10%, egg 5%, sugar 3%, butter 1% and baker's yeast 1.5%.

Therefore, the leavened baked goods obtainable by means of as above described process constitute an object of the present invention.

A further object of the present invention is also the use of the products according to the present invention, i.e. flour dough, mixture of the dough with gluten-free flours, leavened baked goods, leavened baked goods suitable to cover nutritional imbalances resulting from gluten-free diet.

Finally, *Lactobacillus sanfranciscensis* DSM22063 and *Lactobacillus plantarum* DSM 22064 lactic acid bacteria represent an object of the present invention.

The present invention now will be described by an illustrative, but not limitative way according to preferred embodiments thereof, with particular reference to enclosed drawings.

FIG. 1 shows N type aminopeptidase (PepN), dipeptidase (PepV) and tripeptidase (PepT) (a), and proline iminopeptidase (PepI), prolidase (PepQ), prolinase (PepR), dipeptidilpeptidase (PepX) (b) activities of *Lactobacillus sanfranciscensis* DPPMA12 (DSM22063) and *Lactobacillus*

*plantarum* DPPMA125 (DSM22064), on Leu-p-NA, Leu-Leu, Leu-Leu-Leu and Pro-p-NA, Val-For-Gly and Gly-For-Wing synthetic substrates, respectively. Lactic acid bacteria used in the study of Rizzello et al. (Rizzello et al., 2007. *Appl. Environ. Microbiol.* 73:4499-4507) were employed as control: *Lactobacillus alimentarius* 15M, *Lactobacillus brevis* 14G, *L. sanfranciscensis* 7A, *Lactobacillus hilgardii* 51B and *L. sanfranciscensis* LS3, LS10, LS19, LS23, LS38 and LS47. The enzymatic activity was expressed as activity unit (U), i.e. enzyme amount necessary to release 1 μmol/min of p-nitroanilide or 1 μmol/min of amino acid for the activities on substrates different from p-nitroanilide.

EXAMPLE 1

Peptidase Activity of Selected Lactic Bacteria

*L. sanfranciscensis* DPPMA12 and *L. plantarum* DPPMA125 from the Culture Collection of the Dipartimento di Protezione delle Piante and Microbiologia Applicata dell'Universita degli Studi di Bari, previously isolated from "sourdoughs", were propagated at 30° C. for 24 h in modified MRS (mMRS), containing, in addition to usual ingredients, 5% maltose and 10% yeast water—final pH 5.6. As control for peptidase activities of lactic bacteria used in the recent publication by Rizzello et al. (Rizzello et al., 2007. *Appl. Environ. Microbiol.* 73:4499-4507) were used: *Lactobacillus alimentarius* 15M, *Lactobacillus brevis* 14G, *L. sanfranciscensis* 7A, *Lactobacillus hilgardii* 51B and *L. sanfranciscensis* LS3, LS10, LS19, LS23, LS38 and LS47.

Cells cultivated for 24 h, harvested by centrifugation (10000 rpm, 4° C.), washed twice in phosphate buffer 50 mM, pH 7.0 and re-suspended in same buffer at 2.5 ($A_{620}$ nm) optical density, corresponding to $10^8$ cfu/ml, were used for enzyme assays. Type N (PepN) aminopeptidase and proline iminopeptidase (PepI) activities, were determined using Leu-p-NA and Pro-p-NA synthetic substrates, respectively. The reaction mixture consisted of: 0.9 ml of K-phosphate buffer 50 mM, pH 7.0 containing dissolved synthetic substrate (final concentration 2 mM) and 100 μl of cellular suspension. The enzymatic activity, expressed as activity unit (U), corresponds to enzyme amount necessary to release 1 μmol/min of p-nitroanilide (Gobbetti et al., 1996. The proteolytic system of *Lactobacillus sanfranciscensis* CB1: purification and characterization of a proteinase, a dipeptidase, and an aminopeptidase. *Appl. Environ. Microbiol.* 62: 3220-3226). Prolidase (PepQ), prolinase (PepR) and dipeptidil-peptidase (PepX) were determined as described by Cagno and co-workers, (Di Cagno et al., 2004. Sour dough bread made from wheat and nontoxic flours and starter with selected lactobacilli is tolerated in celiac sprue patients, *Appl. Environ. Microbiol.* 70: 1088-1096) on, respectively, Val-Pro, Pro-Gly and Gly-Pro-Ala. Dipeptidase (PepV) and tripeptidase (PepT) were determined according to Cd-ninidrine method (Gobbetti et al., 1999. Study of the effects of temperature, pH, NaCl, and aw on the proteolytic and lipolytic activities of cheese-related lactic bacteria by quadratic response surface methodology, *Enzyme Microbial Technol* 25: 795-809) using, respectively, Leu-Leu and Leu-Leu-Leu. One activity unit (U) is defined as the enzyme amount necessary to release 1 μmol/min of amino acid.

For comparative purposes, the test was repeated also for the lactic bacteria described in WO2008/010252 (*L. sanfranciscensis* LS40, LS13, LS44, LS35, LS14, LS11, LS18, LS4, LS15 and LS41).

EXAMPLE 2

Protein Extraction from Wheat Flour and Electrophoretic Analysis

Proteins were extracted from wheat flour according to method described by Weiss et al. (Weiss et al., 1993. Electrophoretic characterization of wheat grain alergens from different cultivars involved in bakers asthma. *Electrophoresis.* 14:805-816). Bi-dimensional electrophoretic analysis of ca. 30 μg of extracted fraction protein was carried out according to immobiline-polyacrilamide method (De Angelis et al., 2005. *Biochim. Biophys. Acta.* 1762:80-93). Four gels for each independent fermentation were analyzed and data were normalized according to procedure as proposed by Bini et al. (Bini et al., 1997. Protein expression profiles in human breast ductal carcinoma and histologically normal tissue. *Electrophoresis.* 18:2831-2841).

EXAMPLE 3

Immunological and Mass Spectrometry MALDI-TOF Analyses

Immunological analyses were carried out by using of R5 antibody, and sandwich and competitive ELISA test (Transia Plate, Diffchamb) (Valdez et al., 2003. Innovative approach to low-level gluten determination in foods using sandwich enzyme-linked immunosorbent assay protocol. *Eur. J. Gastroenterol. Hepatol.* 15:465-474). MALDI-TOF spectrometry analysis was carried using Voyager-De Pro-workstation (PerSeptive Biosystems United Kingdom) according to method reported by Hernando et al. (Hernando et al., 2003. New strategy for the determination of gliadin in maize or rice-based foods matrix-assisted laser desorption/ionization time-of-flight mass spectrometry fractionation of gliadin from maize or rice-prolamins by acid treatment. *J. Mass Spectrom.* 38:862-871).

Protein concentration was determined according to Bradford method (Bradford, 1976. A rapid and sensitive method for the quantification of microgram quanties of protein utilizing the principle of protein-dye binding. *Anal. Biochem.* 72:248-254). Organic nitrogen concentration was determined according to Kjeldahl method. Free amino acid concentration was determined using an amino acid analyzer (Biochrom Ltd., Cambridge Science Park, United Kingdom) (Di Cagno et al., 2004. *Appl. Environ. Microbiol.* 70:1088-1096).

For comparative purposes, free amino acid concentration was determined also in dough obtained using lattobacilli described in WO2008/010252 (*L. sanfranciscensis* LS40, LS13, LS44, LS35, LS14, LS11, LS18, LS4, LS15 and LS41) after fermentation for 24 hours at 30° C. according to procedures as indicated in the protocol reported in FIG. 8 of said document.

EXAMPLE 4

Manufacture of Leavened Baked Goods Using Detoxified Wheat Flour

Cultures of two selected lactic acid bacteria were propagated in culture medium, washed and re-suspended in water as previously described. Wheat flour was mixed at 30% with water (70%) containing the mixture of said two lactic acid bacteria at a cell density of ca. $10^8$ cfu/g, and fungal enzymes, each at 400 ppm concentration, were added. Fermentation was carried out for 12 h at 37° C. After fermentation, directly to liquid dough native maize (10%), rice flour (10%), egg (5%), sugar (3%), butter (1%) and baker's yeast (1.5%) were added. The concentrations are based on the total dough weight. After kneading, the fermentation is allowed for 1.5 h at 30° C., before the baking of leavened dough for 50 minutes at 250° C.

The process can further comprise a drying step of liquid wheat flour dough. Different ingredients were also used for the production of gluten-free bread.

For comparison purposes also breads 1, 2, 4 and 5 were produced according to the protocol of Patent Application WO2008/010252. Sensory analysis of breads obtained according to the invention and known art, respectively, was carried out, particularly the following descriptors were considered: elasticity, acid fragrance, acid taste, sweetness, dryness and fragrance. Each descriptor was evaluated according to a score scale from 0 to 100. The results of sensory analysis were processed by Principal Component Analysis. Moreover, the breads were analyzed for specific volume, crumb structure, stiffness and fibre content according to standard methods of the American Association of Cereal Chemistry (AACC).

EXAMPLE 5

Administration to Celiac Patients of Leavened Baked Goods Made of Detoxified Wheat Flour Baked goods based on detoxified wheat flour, obtained as previously described, were administered to 5 celiac patients. Opportunely the celiac pathology diagnosis has been acquired according to criteria as proposed by the European Society for Pediatric Gastroenterology, Hepatology and Nutrition. Patient average age was ca. 15 years. Celiac patients were under remission conditions since at least two years and subjected to a controlled gluten-free diet. All patients at recruitment showed serological pathology negative indicators, as well as negative histochemical assays. Each patient, during a 60 day period, daily consumed baked goods which contained detoxified wheat flour corresponding to 10 g of native gluten equivalent. Immunochemical and histological assays were carried out at the Dipartimento di Pediatria e Gastroeneterologia dell'Universita degli Studi di Napoli, Federico II. Patient recruitment occurred with informed consent of the parents to which the experimental schedule, previously approved by the Ethical Committee of the University of Naples, has been subjected.

Results (1) Peptidase Activity of Selected Lactic Acid Bacteria

Figure 1:
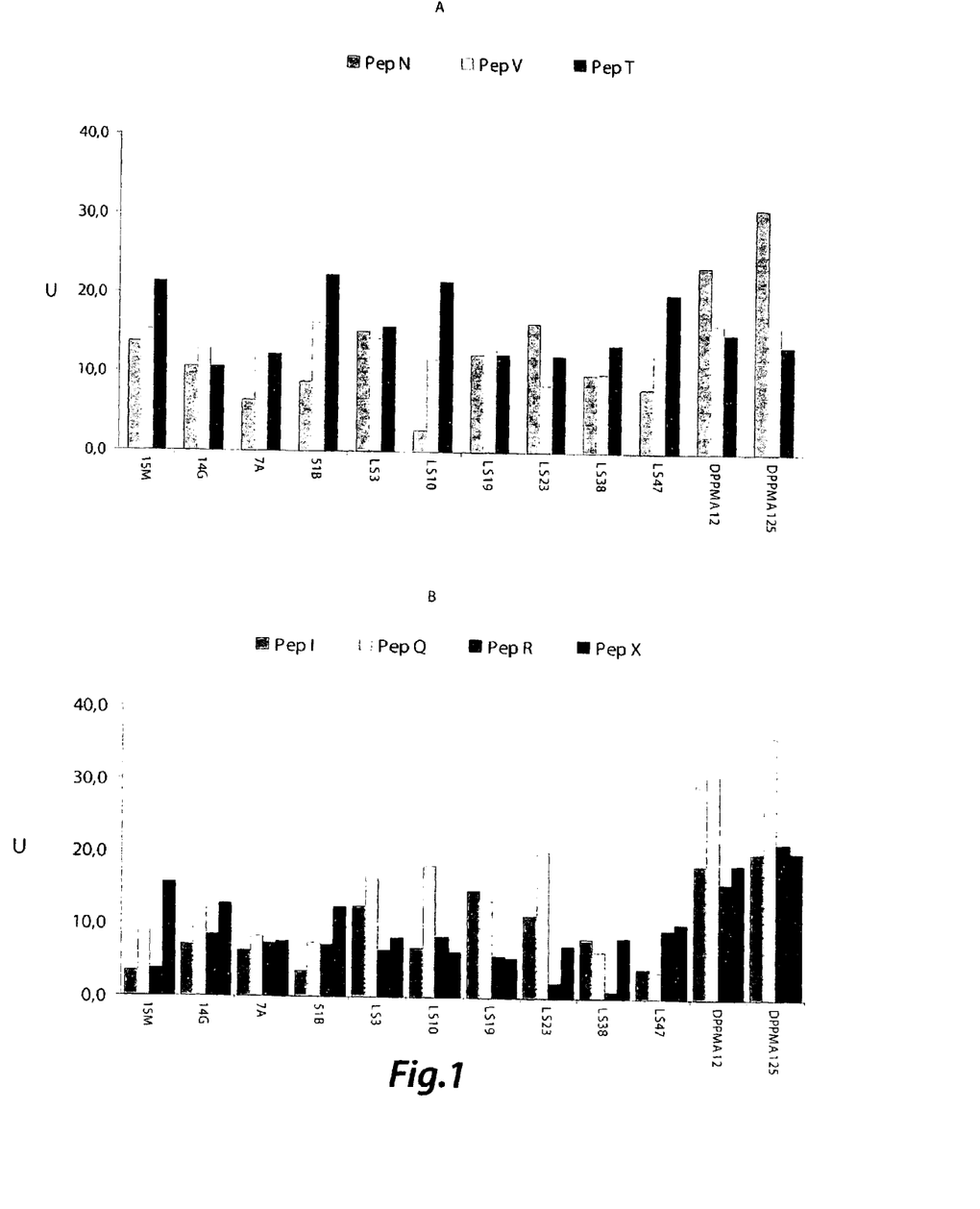

Peptidase activity was assayed on synthetic substrates relatively specific for peptidase activities which are important for the degradation of gluten derived oligopeptides (FIG. 1). It is possible to observe that *L. sanfranciscensis* DPPMA12 and *L. plantarum* DPPMA125 display all the considered enzymatic activities. With the exception of tripeptidase (PepT) type activity, two selected lactic acid bacteria, and particularly *L. plantarum* DPPMA125, display values for other peptidase activities significantly ($P<0.05$) higher than biotypes used in the study by Rizzello et al. (Rizzello et al., 2007. *Appl. Environ. Microbiol.* 73:4499-4507). Significant differences, particularly for PepI, PepQ, PepR and PepX activities, with the presence of proline residues at various bond positions, were detected. Glutenin and in particular gliadins, contain a very high and unusual percentage (45-60%) of glutamine and proline residues. This last iminoacid, consequently, particularly occurs in toxic epitopes, resulting from wheat flour, and responsible of celiac pathology. To provide for microorganisms suitable for high degradation of bond where proline is involved in, this enzyme activity is certainly a pre-requirement for intense gluten degradation and rapid hydrolysis process. The availability of a large Culture Collection to be screened and the large number of assayed enzymatic activities represent, therefore, the requirement to get not commonly available selected strains. Peptidase activity of selected lactic bacteria is enhanced by the complementary use of fungal proteases routinely used in bread-making processes. Such enzymes are employed in the bread-making industry in order to modify the protein concentration and, therefore, the "flour strength", depending on baked goods they are designed to.

Figure 4:
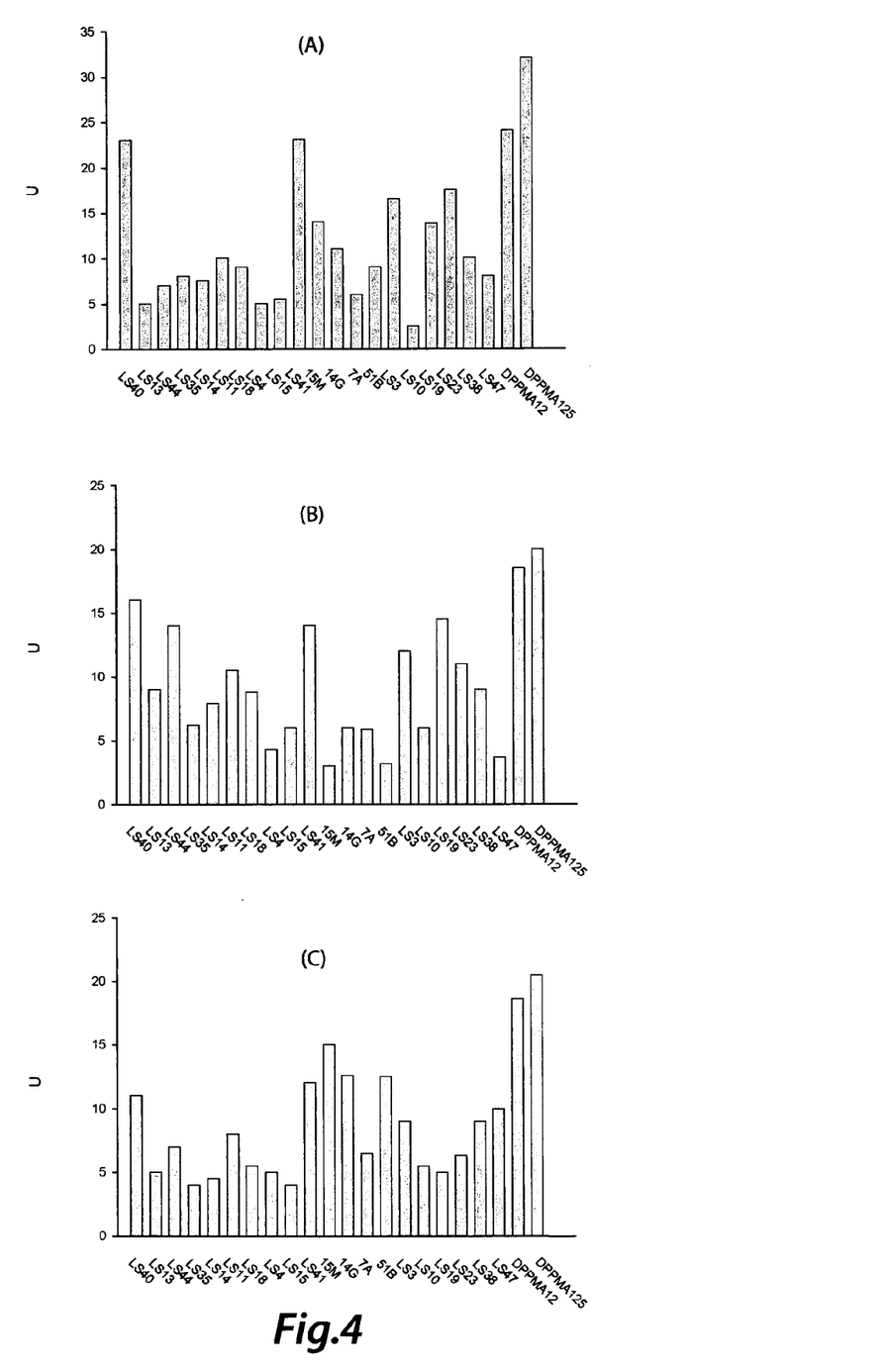
FIG. 4 shows aminopeptidase (A), proline iminopeptidase (B) and prolyl-dipeptidil aminopeptidase (C) activities of lactic acid bacteria used according to WO2008/010252 (*Lactobacillus sanfranciscensis* LS40, LS13, LS44, LS35, LS14, LS11, LS18, LS4, LS15 and LS41) and the present invention [*L. sanfranciscensis* DPPMA12 (DSM22063) and *Lactobacillus plantarum* DPPMA125 (DSM22064)]. The acronyms 15M, 14G, 7A, 51B, LS3, LS10, LS19 LS23, LS38 and LS47 stand for biotypes as used according to Rizzello et al., 2007, publication.

FIG. 4 shows a comparison of peptidase activities for known art lactic acid bacteria and two lactic acid bacteria (DPPMA12 and DPPMA125) according to the invention, respectively, and it is apparent that the latter display markedly higher aminopeptidase, proline iminopeptidase and prolyl-dipeptidil aminopeptidase activities.

(2) Characterization of Hydrolised Flour

Figure 2:
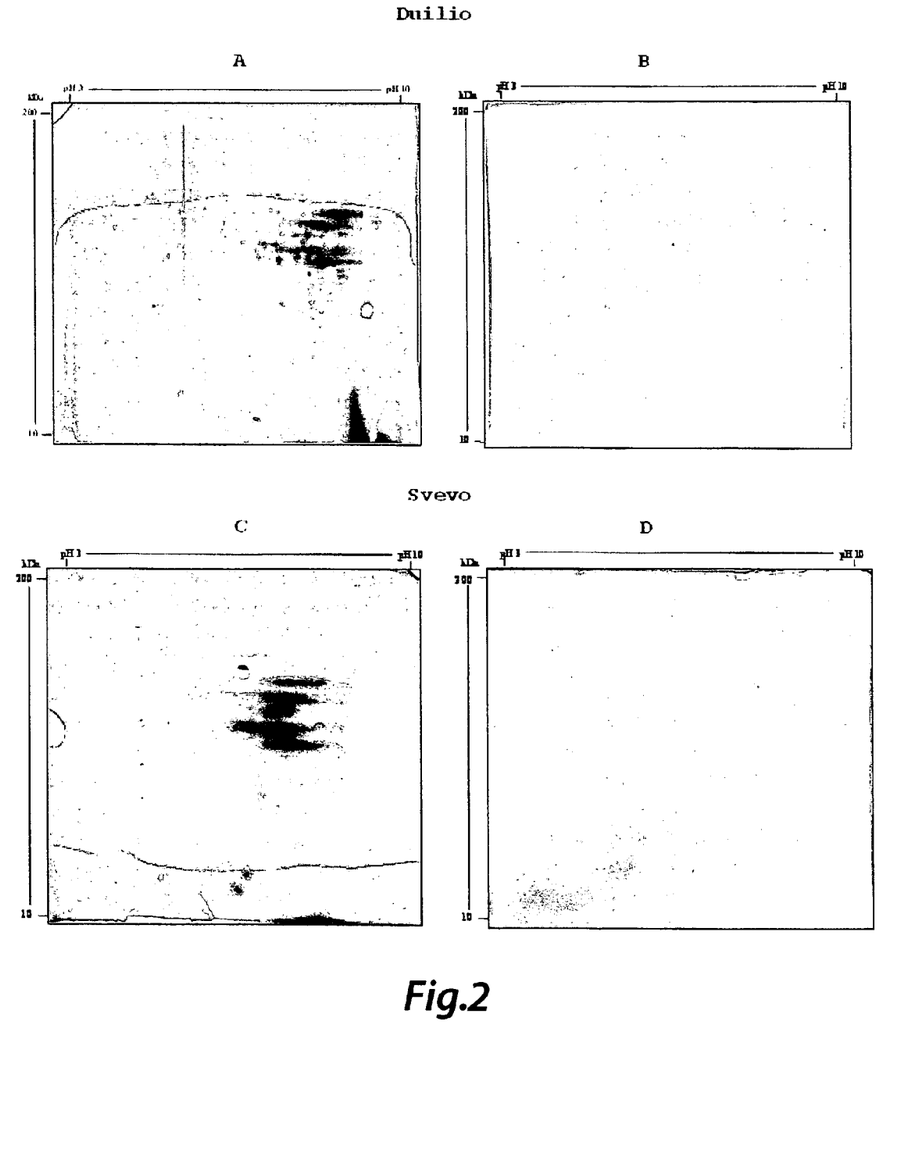
FIG. 2 shows bi-dimensional electrophoretic profiles of various durum wheat varieties (Svevo and Duilio) before and after treatment with selected lactic acid bacteria and fungal proteases.

After fermentation for 12 h at 37° C., protein fractions were selectively extracted and subjected to complementary analytical assays. As it is apparent using bi-dimensional electrophoretic analysis (FIG. 2), at the end of fermentation process no traces of gliadins from Svevo and Duilio durum wheat variety flours are detectable. Similar results were found in the glutenin fraction for bread commercially available "00" type wheat, other durum wheat tested varieties (Arcangelo, Ciccio, Colosseo, Gargano and Simeto) and barley, rye and oat flours. Wheat flour proteins, extracted with 60% ethanol, were analyzed with MALDI-TOF MS technique. Peaks corresponding to gliadin European standard completely disappeared after fermentation for 12 h at 37° C. Only some peaks with molecular mass lower than 8 kDa were detected by spectrometry analysis. Immunological analyses carried out using R5 antibodies and ELISA assays confirmed that no gliadin traces were detectable in fermented sample. According to same method the residual gluten concentration determined in bread commercially available type "00" wheat, durum wheat variety and barley, rye and oat flours was, in all the cases, lower than 20 ppm. The method used for these determinations is an AIC (Associazione Italiana Celiachia), WHO and FAO official method. With respect to literature reported data (Rizzello et al., 2007. *Appl. Environ. Microbiol.* 73:4499-4507), the hydrolysis process is carried out with the same effectiveness (residual gluten <20 ppm) but in a markedly shorter times (12 versus 48 h). This process high rate results, on the one hand, from the use of higher concentration of each of fungal proteolytic enzymes (400 ppm) and, on the other hand, mainly from higher peptidase activity of selected lactic bacteria biotypes. Again in comparison to said literature reference which only considered bread wheat flour with low initial gluten concentration, the present invention shows the protocol effectiveness also on various durum wheat varieties, and barley, rye and oat flours having also initial elevated protein concentrations.

Figure 3:
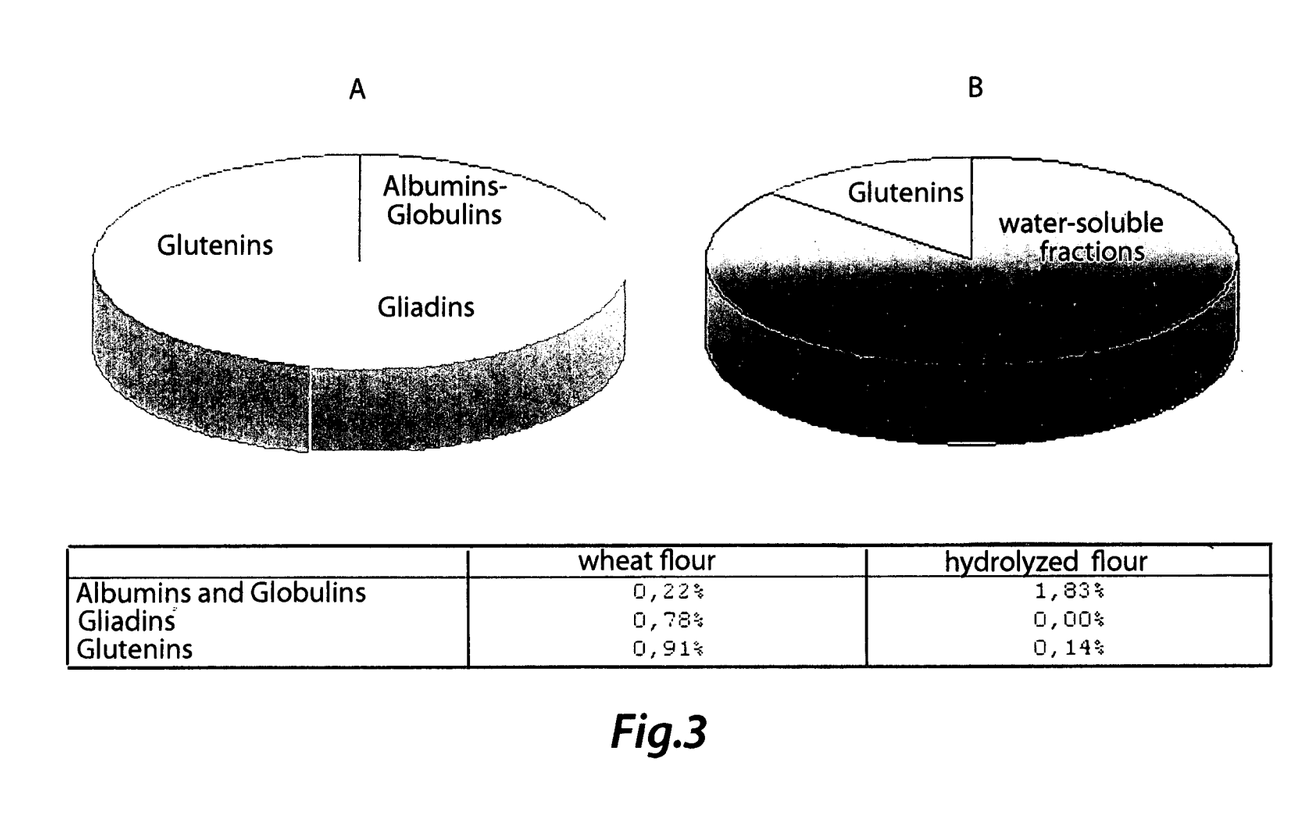
FIG. 3 shows the protein composition of wheat flour before and after the hydrolysis process by selected lactic acid bacteria and fungal proteases.

In FIG. 3 organic nitrogen content of bread commercially available type "00" wheat flour before and after the fermentation process is reported. Hydrolysed flour almost totally consists of a mixture of low molecular weight peptides and amino acids. Only an amount lower than 20% of initial glutenins is yet present in hydrolysed flour. Amino acid concentration in hydrolysed flour is about 15000 mg/kg compared to <1.000 mg/kg occurring in wheat flour. Higher bioavailability of free amino acids makes this hydrolysed wheat flour a raw material with high nutritional content, retaining at the same time other cereal nutritional characteristics in terms of mineral salts, vitamins and fibres. Where used as an ingredient for the production of gluten-free foods, the hydrolysed wheat flour would cover nutritional imbalances resulting from gluten-free diet (Grehn et al., 2001. *Scand J Nutr* 45: 178-182; Mariani et al., 1998. *J Pediart Gastroenterol Nut* 27: 519-523; Thompson et al., 2005. *J. Human. Nutr. Diet.* 18:163-169)

Figure 6:
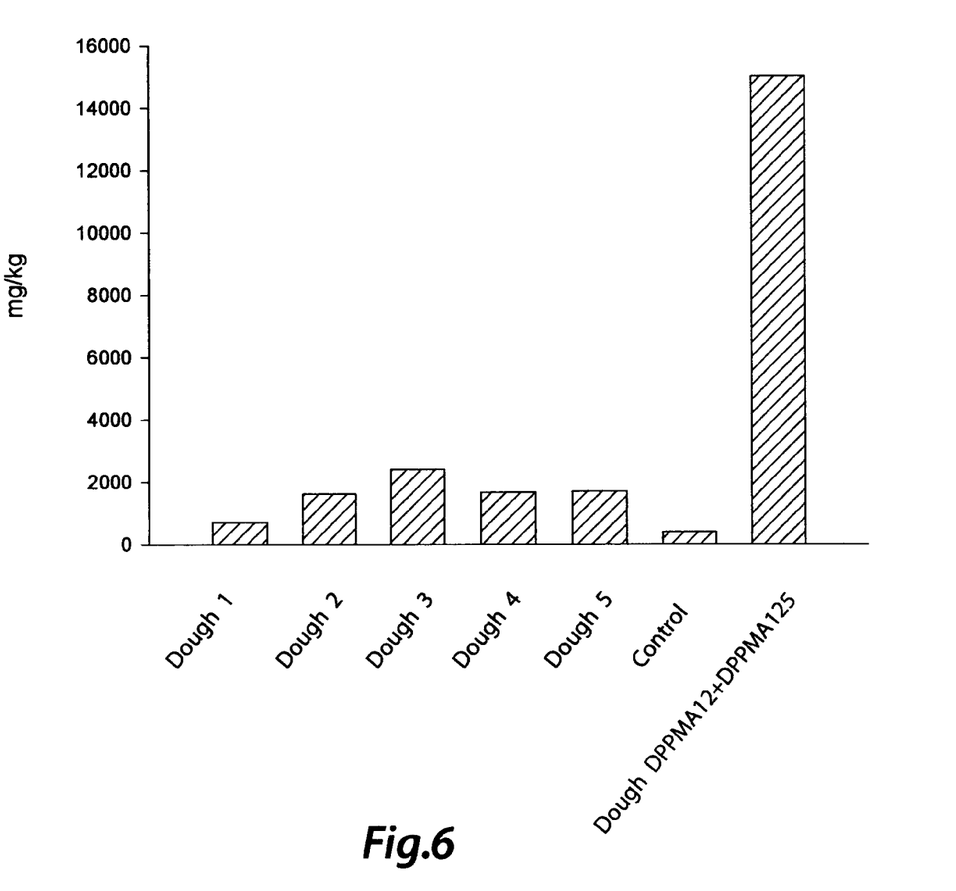
FIG. 6 shows the concentration of total free amino acids (mg/kg) in fermented dough using different combinations of lactic bacteria according to WO2008/010252 (dough 1, 2, 3, 4 and 5) and wheat flour dough fermented with two lactic acid bacteria (DDPPMA12 and DPPMA125) of the present invention.

Comparative test with known art lactic acid bacteria shows that the amino acid concentration in the dough is remarkably lower and equal to about 2000 mg/kg after highest hydrolysis condition (FIG. 6). This confirms the different hydrolysis degree of wheat proteins. Moreover, since released amino acids are precursors of volatile compounds which are generated during baking process and are responsible for baked goods taste, remarkably higher free amino acid concentration, as in the case of the present invention, indicates higher synthesis of volatile compounds and, therefore, a better taste of the products according to the invention.

(3) Production of Leavened Baked Goods Using Detoxified Wheat Flour

An application example of biotechnological protocol for the manufacture of leavened baked goods based on detoxified wheat flour was reported above. In addition to the manufacture of baked goods, the protocol was standardized and optimized also for gluten-free bread production with previously described ingredients. In addition to the possible direct use of detoxified wheat flour, a treatment thereof using spry-drier and subsequent use as dried matter is possible. This further technological possibility allows an easy conservation of the raw material over the time, without any alteration of wheat flour nutritional characteristics.

Figure 7:
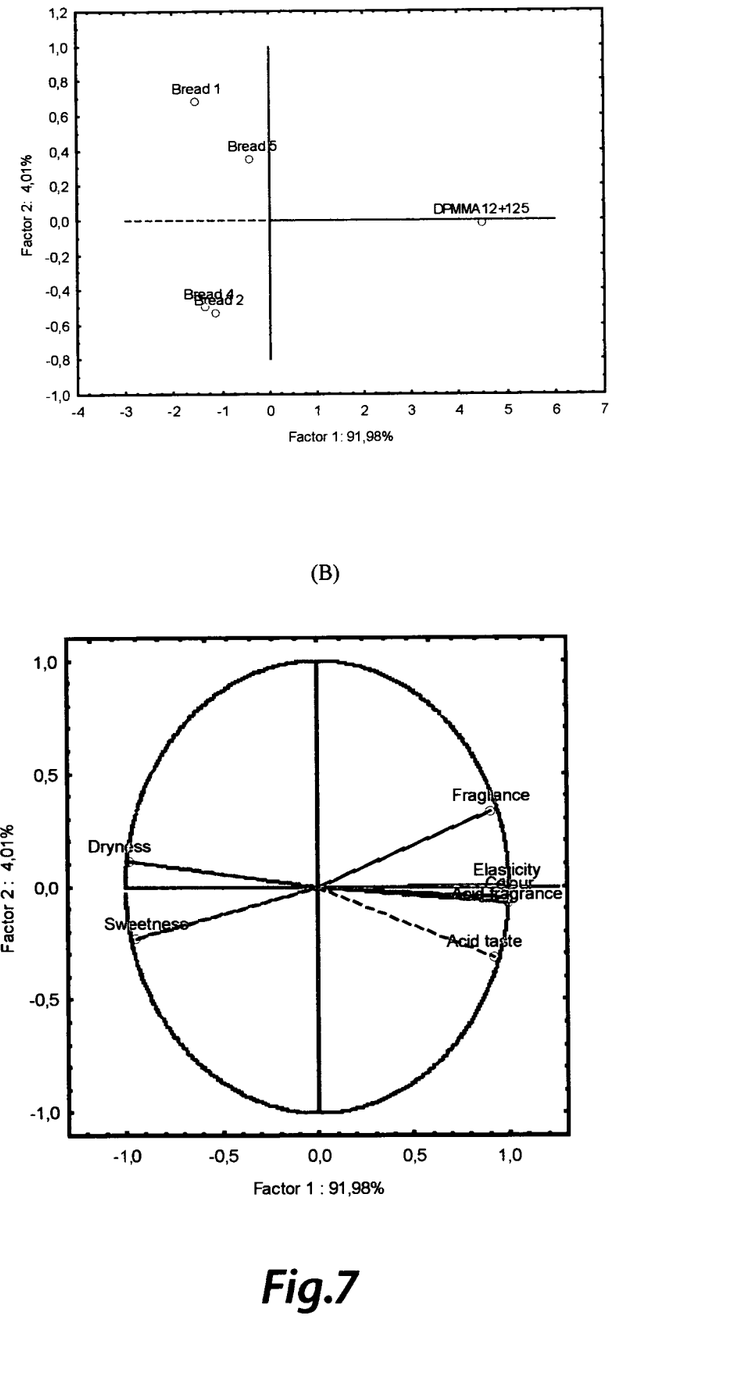
FIG. 7 shows the Principal Component Analysis (PCA) of the data obtained from sensory analysis of breads (1, 2, 4 and 5) according to WO2008/010252 and bread (DPPMA12 and DPPMA125) obtained using detoxified wheat flour according to the invention.

FIG. 7 shows the best sensory properties of the bread according to the present invention (DPPMA12+DPPMA125) compared to known art breads. Moreover, table 1 shows that the bread according to the present invention is characterized by higher specific volume, more crumb bubbles, lower stiffness, and higher fibre content compared to known art bread. These differences result from the presence of wheat flour that although detoxified is suitable to favour better rheological and chemical characteristics.

TABLE 1

| Rheological and chemical parameters | Bread Starter 1* | Bread (DPPMA12 + DPPMA125) |
|---|---|---|
| Specific volume (cm3/g) | 1.35 ± 0.04 | 1.48 ± 0.07 |
| Crumb bubbles (%) | 39.2 ± 0.34 | 42.3 ± 0.47 |
| Stiffness (n) | 16.62 ± 0.27 | 14.75 ± 0.21 |
| Fibre content (%) | 1.5 ± 0.44 | 2.0 ± 0.52 |

*Lactobacillus sanfranciscensis DSM18426, DSM18427, Lactobacillus plantarum DSM18430

(4) Administration to Celiac Patients of Baked Goods Made of Detoxified Wheat Flour Baked goods prepared according to previously described biotechnological protocol have been administered daily to celiac patients corresponding to a dose equivalent to 10 g of native gluten. In Table 2 immunochemical and histological indices of in remission celiac patients subjected to consumption (10 g of gluten equivalent to the day for 60 gg) based on detoxified wheat flour are reported.

TABLE 2

| | Anti-tTG | | Immunochemistry | | | | | | Marsh Grade | |
|---|---|---|---|---|---|---|---|---|---|---|
| | | | CD3 | | CD25 | | $\gamma^\delta$ | | | |
| | $T_0$ | $T_{60}$ | $T_0$ | $T_{60}$ | $T_0$ | $T_{60}$ | $T_0$ | $T_{60}$ | $T_0$ | $T_{60}$ |
| F. I. | 1.6 | 1 | 39 | 38 | 6 | 5 | 5.6 | 8.6 | 0 | 0 |
| I. C. | 1.9 | 1.1 | 3.7 | 11 | 11 | 9 | 0.9 | 3.8 | 0 | 0 |
| R. R. | 0.3 | 0.3 | 53 | 56 | 3 | 4 | 11.5 | 17.8 | 1 | 1 |
| I. I. | 0.5 | 0.3 | 31 | 36 | 21 | 21 | 8.4 | 12.8 | 0 | 0 |

As it is possible to observe, all the patients at recruitment time ($T_0$) display normal serological and histological values (Marshes Grade). After each daily assumption of 10 g gluten equivalent, over a 60 day period ($T_{60}$), none of biochemical and immunohistochemical values was different compared to initial value. In particular, it is to be observed that Marsh Grade, who represents the integrity condition and functionality of the intestinal mucosa, as detected based on bio-optical sample, is absolutely identical to initial value. No patient developed atrophy of intestinal villas during the challenge. Only one out 5 recruited patients interrupted the test due to personal reasons and not depending on eventual pathological condition. On the base of acquired results based on most careful in vivo clinical analyses, it is possible to state that the detoxified wheat flour was tolerated by all the patients. In conclusion, detoxified wheat flour can be used for the preparation of gluten-free foods.

The invention claimed is:

1. A process for preparation of a liquid sourdough in which gluten is completely degraded and which is suitable for use in production of leavened gluten-free products, comprising:
   a) culture propagating of *Lactobacillus sanfranciscensis* DSM22063 and *Lactobacillus plantarum* DSM 22064 lactic acid bacteria;
   wherein the lactic acid bacteria of step a) each have an x-prolyl dipeptidyl aminopeptidase activity of between 17.5 U and 22 U, U being defined as the enzyme amount necessary to release 1 µmol/min of amino acid;

b) mixing flour, water and the culture of step a),
wherein the flour is about 20-50 wt % of the resulting mixture of step b), the water is about 50-80 wt % of the resulting mixture of step b) and the culture of step a) has a cellular density of about $10^8$ cfu/g; and
wherein the flour is at least one gluten-containing flour selected from the group consisting of bread wheat, durum wheat, tender wheat, barley, rye and oat flours;
c) adding at least one fungal protease into the resulting mixture of step b), wherein at least one of the protease has a final concentration of about 200-500 ppm; and
d) incubating the resulting mixture of step c) for 8-20 h, at 30-37° C. to obtain the liquid sourdough.

2. The process according to claim 1, further comprising a step e) of drying the liquid sourdough obtained in step d).

3. The process according to claim 1, wherein the fungal protease is at least one selected from the group consisting of *Aspergillus oryzae* and *Aspergillus niger* proteases.

4. The process according to claim 1, wherein the flour is about 30 wt % of the resulting mixture of step b), and the water is about 70 wt % of the resulting mixture of step b).

5. The process according to claim 1, wherein each of the proteases has a final concentration of about 200-500 ppm.

6. The process according to claim 1, wherein at least one of the proteases has a final concentration of about 400 ppm.

7. The process according to claim 1, wherein the incubation of step d) lasts for 12 h.

* * * * *